(12) United States Patent
Annest et al.

(10) Patent No.: US 9,402,722 B2
(45) Date of Patent: *Aug. 2, 2016

(54) STEERABLE LESION EXCLUDING HEART IMPLANTS FOR CONGESTIVE HEART FAILURE

(71) Applicant: BioVentrix, Inc., San Ramon, CA (US)

(72) Inventors: Lon S. Annest, New York, NY (US); Arthur A. Bertolero, Danville, CA (US); Sing-Fatt Chin, Fremont, CA (US); David K. Swanson, Campbell, CA (US)

(73) Assignee: BioVentrix, Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/723,187

(22) Filed: May 27, 2015

(65) Prior Publication Data

US 2016/0022422 A1  Jan. 28, 2016

Related U.S. Application Data

(63) Continuation of application No. 13/794,096, filed on Mar. 11, 2013, now Pat. No. 9,044,231, which is a continuation of application No. 12/846,777, filed on Jul. 29, 2010, now Pat. No. 8,394,008, which is a
(Continued)

(51) Int. Cl.
*A61N 1/362* (2006.01)
*A61F 2/24* (2006.01)
(Continued)

(52) U.S. Cl.
CPC ......... *A61F 2/2487* (2013.01); *A61B 17/00234* (2013.01); *A61B 17/0401* (2013.01); *A61B 17/0487* (2013.01); *A61B 17/08* (2013.01); *A61B 17/0467* (2013.01); *A61B 2017/003* (2013.01); *A61B 2017/00022* (2013.01); *A61B 2017/00247* (2013.01); *A61B 2017/00867* (2013.01);
(Continued)

(58) Field of Classification Search
CPC ............. A61B 17/08; A61B 17/00234; A61B 17/0401; A61N 1/362
USPC ...................................... 600/16–18
See application file for complete search history.

(56) References Cited

U.S. PATENT DOCUMENTS

| 4,007,743 | A | 2/1977 | Blake |
| 5,295,958 | A | 3/1994 | Shturman |

(Continued)

FOREIGN PATENT DOCUMENTS

| EP | 1078644 A1 | 2/2001 |
| WO | 00-06028 A1 | 2/2000 |

(Continued)

OTHER PUBLICATIONS

European Examination Report of EP Patent Application 05810316.9 dated Mar. 10, 2009, 6 pages.

(Continued)

*Primary Examiner* — John Lacyk
(74) *Attorney, Agent, or Firm* — Kilpatrick Townsend & Stockton LLP

(57) ABSTRACT

Devices, systems, and methods for treating a heart of a patient may make use of one or more implant structures which limit a size of a chamber of the heart, such as by deploying a tensile member to bring a wall of the heart toward (optionally into contact with) a septum of the heart.

20 Claims, 11 Drawing Sheets

Related U.S. Application Data continuation of application No. 12/033,641, filed on Feb. 19, 2008, now Pat. No. 7,785,248, which is a continuation of application No. PCT/US2006/032663, filed on Aug. 21, 2006.

(60) Provisional application No. 60/709,730, filed on Aug. 19, 2005.

(51) Int. Cl.
| | |
|---|---|
| *A61B 17/00* | (2006.01) |
| *A61B 17/04* | (2006.01) |
| *A61B 17/08* | (2006.01) |
| *A61B 17/06* | (2006.01) |
| *A61B 17/22* | (2006.01) |
| *A61B 18/00* | (2006.01) |

(52) U.S. Cl.
CPC . *A61B2017/00986* (2013.01); *A61B 2017/048* (2013.01); *A61B 2017/0412* (2013.01); *A61B 2017/0417* (2013.01); *A61B 2017/0462* (2013.01); *A61B 2017/0464* (2013.01); *A61B 2017/0496* (2013.01); *A61B 2017/06052* (2013.01); *A61B 2017/06176* (2013.01); *A61B 2017/22054* (2013.01); *A61B 2017/22069* (2013.01); *A61B 2018/00392* (2013.01)

(56) References Cited

U.S. PATENT DOCUMENTS

| | | | |
|---|---|---|---|
| 5,336,252 A | 8/1994 | Cohen | |
| 5,482,037 A | 1/1996 | Borghi | |
| 5,755,697 A | 5/1998 | Jone et al. | |
| 5,810,884 A | 9/1998 | Kim | |
| 5,830,224 A | 11/1998 | Cohn et al. | |
| 5,865,730 A | 2/1999 | Fox et al. | |
| 5,961,440 A | 10/1999 | Schweich, Jr. et al. | |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,080,182 A | 6/2000 | Shaw et al. | |
| 6,125,852 A | 10/2000 | Stevens et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,166,684 A | 12/2000 | Yoshikawa et al. | |
| 6,258,021 B1 | 7/2001 | Wilk | |
| 6,260,552 B1 | 7/2001 | Mortier et al. | |
| 6,406,420 B1 | 6/2002 | McCarthy et al. | |
| 6,494,825 B1 | 12/2002 | Talpade | |
| 6,511,416 B1 | 1/2003 | Green et al. | |
| 6,572,529 B2 | 6/2003 | Wilk | |
| 6,616,684 B1 | 9/2003 | Vidlund et al. | |
| 6,623,508 B2 | 9/2003 | Shaw et al. | |
| 6,705,988 B2 | 3/2004 | Spence et al. | |
| 6,709,382 B1 | 3/2004 | Horner | |
| 6,723,038 B1 | 4/2004 | Schroeder et al. | |
| 6,746,471 B2 | 6/2004 | Mortier et al. | |
| 6,776,754 B1 | 8/2004 | Wilk | |
| 6,808,488 B2 | 10/2004 | Mortier | |
| 6,859,662 B2 | 2/2005 | Bombardini | |
| 6,890,295 B2 | 5/2005 | Michels et al. | |
| 7,146,225 B2 | 12/2006 | Guenst et al. | |
| 7,326,177 B2 | 2/2008 | Williamson | |
| 7,390,329 B2 | 6/2008 | Westra et al. | |
| 7,431,691 B1 | 10/2008 | Wilk | |
| 7,637,924 B2 | 12/2009 | Gifford et al. | |
| 7,722,523 B2 | 5/2010 | Mortier et al. | |
| 7,753,923 B2 | 7/2010 | St. Goar et al. | |
| 7,766,816 B2 | 8/2010 | Chin et al. | |
| 7,785,248 B2 | 8/2010 | Annest et al. | |
| 7,942,854 B1 | 5/2011 | Von Oepen et al. | |
| 8,066,766 B2 | 11/2011 | To et al. | |
| 8,123,668 B2 | 2/2012 | Annest et al. | |
| 8,268,009 B2 | 9/2012 | Teitelbaum et al. | |
| 8,394,008 B2* | 3/2013 | Annest | A61B 17/00234 600/16 |
| 8,425,402 B2 | 4/2013 | Annest et al. | |
| 8,449,442 B2 | 5/2013 | Annest et al. | |
| 8,491,455 B2 | 7/2013 | Annest et al. | |
| 8,506,474 B2 | 8/2013 | Chin et al. | |
| 8,636,639 B2 | 1/2014 | Annest et al. | |
| 8,968,175 B2 | 3/2015 | Annest et al. | |
| 8,979,750 B2 | 3/2015 | Bladel et al. | |
| 8,986,189 B2 | 3/2015 | Chin et al. | |
| 9,039,594 B2 | 5/2015 | Annest et al. | |
| 9,044,231 B2* | 6/2015 | Annest | A61B 17/00234 |
| 9,095,363 B2 | 8/2015 | Bladel et al. | |
| 9,119,720 B2 | 9/2015 | Chin et al. | |
| 9,173,711 B2 | 11/2015 | Butler et al. | |
| 9,173,712 B2 | 11/2015 | Annest et al. | |
| 9,211,115 B2 | 12/2015 | Annest et al. | |
| 9,259,319 B2 | 2/2016 | Chin et al. | |
| 2001/0025171 A1 | 9/2001 | Mortier et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0077655 A1 | 6/2002 | Frova | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2002/0198563 A1 | 12/2002 | Gainor et al. | |
| 2003/0032979 A1 | 2/2003 | Mortier et al. | |
| 2003/0163165 A1 | 8/2003 | Bornzin et al. | |
| 2003/0166992 A1 | 9/2003 | Schweich, Jr. et al. | |
| 2003/0181928 A1 | 9/2003 | Vidlund et al. | |
| 2003/0181951 A1 | 9/2003 | Cates | |
| 2003/0220587 A1 | 11/2003 | Swenson | |
| 2003/0233022 A1 | 12/2003 | Vidlund et al. | |
| 2004/0064143 A1 | 4/2004 | Hicken et al. | |
| 2004/0082837 A1 | 4/2004 | Willis | |
| 2004/0088035 A1 | 5/2004 | Guenst et al. | |
| 2004/0167374 A1 | 8/2004 | Schweich | |
| 2004/0167580 A1 | 8/2004 | Mann et al. | |
| 2004/0225304 A1 | 11/2004 | Vidlund et al. | |
| 2004/0267306 A1 | 12/2004 | Blaeser et al. | |
| 2005/0065506 A1 | 3/2005 | Phan | |
| 2005/0075723 A1 | 4/2005 | Schroeder et al. | |
| 2005/0096498 A1 | 5/2005 | Houser et al. | |
| 2005/0137688 A1 | 6/2005 | Salahieh et al. | |
| 2005/0143620 A1 | 6/2005 | Mortier et al. | |
| 2005/0149115 A1 | 7/2005 | Roue et al. | |
| 2005/0192599 A1 | 9/2005 | Demarais | |
| 2005/0215851 A1 | 9/2005 | Kim et al. | |
| 2005/0288613 A1 | 12/2005 | Heil | |
| 2006/0004408 A1 | 1/2006 | Morris et al. | |
| 2006/0079736 A1 | 4/2006 | Chin et al. | |
| 2006/0135962 A1 | 6/2006 | Kick et al. | |
| 2006/0161040 A1 | 7/2006 | McCarthy et al. | |
| 2006/0161238 A1 | 7/2006 | Hall | |
| 2006/0167416 A1 | 7/2006 | Mathis et al. | |
| 2006/0178550 A1 | 8/2006 | Jenson | |
| 2006/0200002 A1 | 9/2006 | Guenst | |
| 2006/0241340 A1 | 10/2006 | Schroeder et al. | |
| 2006/0247672 A1 | 11/2006 | Vidlund et al. | |
| 2006/0276684 A1 | 12/2006 | Speziali | |
| 2007/0005018 A1 | 1/2007 | Tkebuchava | |
| 2007/0010876 A1 | 1/2007 | Salahieh et al. | |
| 2007/0049971 A1 | 3/2007 | Chin et al. | |
| 2007/0055303 A1 | 3/2007 | Vidlund et al. | |
| 2007/0073274 A1 | 3/2007 | Chin et al. | |
| 2007/0112244 A1 | 5/2007 | McCarthy et al. | |
| 2007/0161846 A1 | 7/2007 | Nikotic et al. | |
| 2007/0203503 A1 | 8/2007 | Salahieh et al. | |
| 2007/0265658 A1 | 11/2007 | Nelson et al. | |
| 2008/0082132 A1 | 4/2008 | Annest et al. | |

(56) References Cited

U.S. PATENT DOCUMENTS

| | | |
|---|---|---|
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0268020 A1 | 10/2010 | Chin et al. |
| 2011/0160750 A1 | 6/2011 | Annest et al. |
| 2011/0270191 A1 | 11/2011 | Paul et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2014/0350417 A1 | 11/2014 | Bladel et al. |
| 2015/0066082 A1 | 3/2015 | Moshe et al. |
| 2015/0066139 A1 | 3/2015 | Bladel et al. |
| 2015/0238182 A1 | 8/2015 | Annest et al. |
| 2016/0022422 A1 | 1/2016 | Annest et al. |

FOREIGN PATENT DOCUMENTS

| | | |
|---|---|---|
| WO | 02-30335 A2 | 4/2002 |
| WO | 03-032818 A3 | 4/2003 |
| WO | 2004-043267 A2 | 5/2004 |
| WO | 2005-092203 A1 | 10/2005 |
| WO | 2006-044467 A2 | 4/2006 |
| WO | 2007-022519 A2 | 2/2007 |
| WO | 2013-049761 A1 | 4/2013 |

OTHER PUBLICATIONS

Extended European Examination Report of EP Patent Application 06802038.7 dated Nov. 12, 2013, 13 pages.
Office Action of EP Patent Application 06802038.7 dated Sep. 11, 2014, 4 pages.
International Report on Patentability of PCT/US2012/058074 dated Apr. 10, 2014, 8 pages.
International Report on Patentability of PCT/US2012/058176 dated Apr. 10, 2014, 11 pages.
International Search Report and Written Opinion of PCT Application No. PCT/US06/22594, mailed Oct. 1, 2008, 4 pages.
International Search Report and Written Opinion of PCT Application No. PCT/US06/32663, Jul. 31, 2007, 5 pages.
International Search Report and Written Opinion of PCT Application No. PCT/US08/64255, mailed Sep. 29, 2008, 13 pages.
International Search Report and Written Opinion of PCT Application No. PCT/US08/78810, mailed Feb. 12, 2009, 9 pages.
International Search Report and Written Opinion of PCT Application No. PCT/US09/51288, mailed Sep. 15, 2009, 7 pages.
International Search Report and Written Opinion of PCT Application No. PCT/US12/58074, mailed Mar. 13, 2013, 18 pages.
International Search Report and Written Opinion of PCT Application No. PCT/US2005/036690, mailed Jul. 9, 2007, 6 pages.
International Search Report and Written Opinion of PCT/US2012/058106, mailed Nov. 26, 2012, 14 pages.
International Search Report and Written Opinion of PCT/US2012/58176, mailed Jan. 8, 2013, 19 pages.
International Search Report and Written Opinion of PCT/US2012/058182, mailed Mar. 1, 2013, 12 pages.
USPTO—STIC Search Results—NPL (Dec. 11, 2014).
USPTO—STIC Search Results—Patents (Dec. 11, 2014).
Internationl Search Report and Written Opinion of PCT Application No. PCT/US2014/053209 mailed Mar. 2, 2015, 18 pages.
International Search Report and Written Opinion of PCT/US2014/038834 mailed Oct. 16, 2014, 16 pages.
International Report on Patentability of PCT/US2014/038834 mailed Dec. 3, 2015, 11 pages.

\* cited by examiner

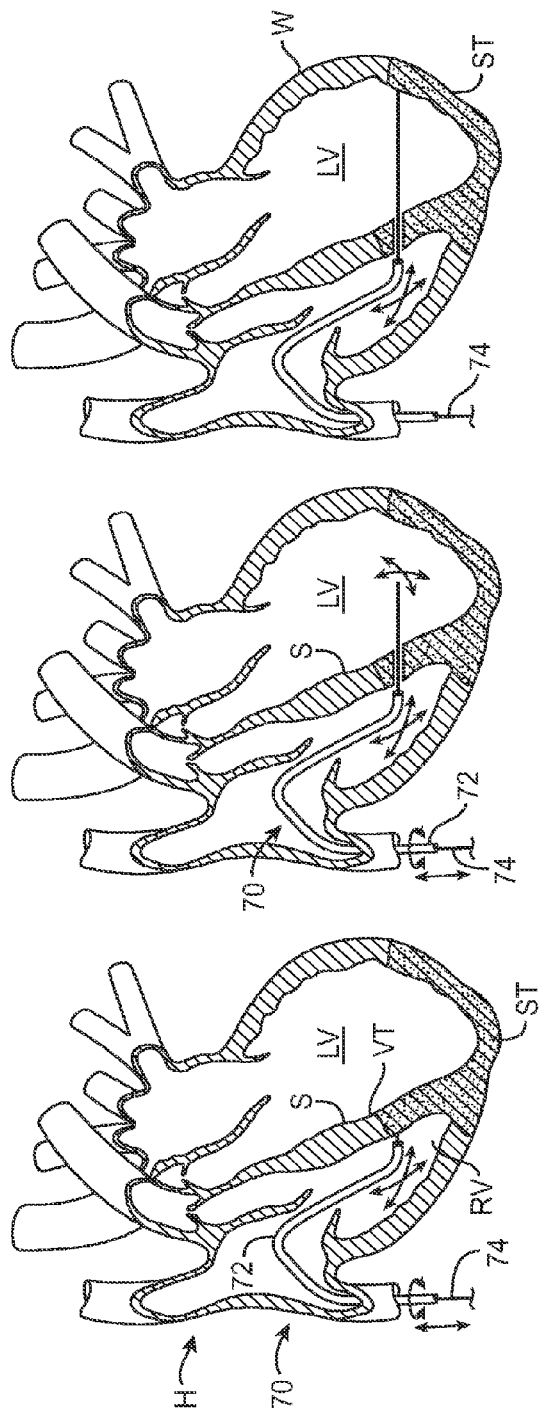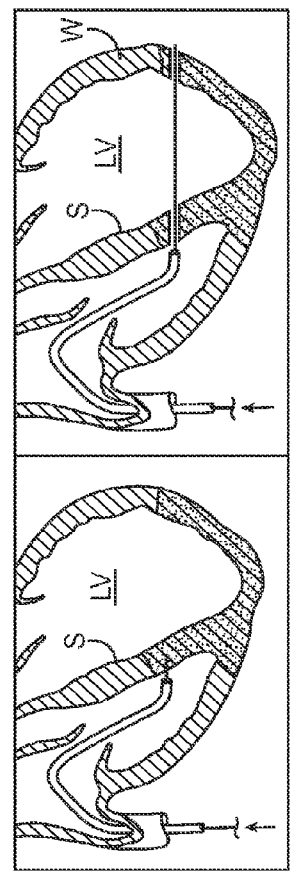

STEERABLE LESION EXCLUDING HEART IMPLANTS FOR CONGESTIVE HEART FAILURE

CROSS-REFERENCES TO RELATED APPLICATIONS

This application is a continuation of U.S. application Ser. No. 13/794,096 filed Mar. 11, 2013 which is a continuation of U.S. application Ser. No. 12/846,777 filed Jul. 29, 2010 which is a continuation of U.S. application Ser. No. 12/033,641 filed Feb. 19, 2008 which is a continuation of PCT Patent Application No. PCT/US2006/032663 filed on Aug. 21, 2006, which claims the benefit of priority from provisional application No. 60/709,730 filed Aug. 19, 2005; the full disclosures of which are incorporated herein by reference in their entirety for all purposes.

BACKGROUND OF THE INVENTION

The present invention is generally directed to improved devices, systems, and methods for treatment of the heart. Exemplary embodiments provide implants and methods for alleviating congestive heart failure and other progressive diseases of the heart. Congestive heart failure may, for example, be treated using one or more implants which is selectively positioned relative to a septum and wall of the heart so as to exclude scar tissue and limit a cross section across a ventricle.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunctions due to rheumatic fever or other causes, cardiomyopathy (a primary disease of the heart muscle itself), congenital heart defects, infections of the heart tissues, and the like. However, in most cases congestive heart failure may be triggered by a heart attack or myocardial infarction. Heart attacks can cause scar tissue that interferes with the heart muscle's healthy function, and that scar tissue can progressively replace more and more of the heart tissue. More specifically, the presence of the scar may lead to a compensatory neuro-hormonal response by the remaining, non-infarcted myocardium.

People with heart failure may have difficulty exerting themselves, often becoming short of breath, tired, and the like. As blood flow out of the heart slows, blood returning to the heart through the vascular system decreases, causing congestion in the tissues. Edema or swelling may occur in the legs and ankles, as well as other parts of the body. Fluid may also collect in the lungs, interfering with breathing (especially when lying down). Congestive heart failure may also decrease the ability of the kidneys to remove sodium and water, and the fluid buildup may be sufficient to cause substantial weight gain. With progression of the disease, this destructive sequence of events can cause the eventual failure of the remaining functional heart muscle.

Treatments for congestive heart failure may involve rest, dietary changes, and modified daily activities. Various drugs may also be used to alleviate detrimental effects of congestive heart failure, such as by expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient trauma. While people with mild or moderate congestive heart failure may benefit from these known techniques to alleviate the symptoms and/or slow the progression of the disease, less traumatic therapies which significantly increase the heart function and extend life of congestive heart failure patients has remained a goal.

It has recently been proposed that an insert or implant be placed in the heart of patients with congestive heart failure so as to reduce ventricular volume. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be constricted or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

An exemplary method and implant for closing off a lower portion of a heart ventricle is shown in FIG. 1, and is more fully described in U.S. Pat. No. 6,776,754, the full disclosure of which is incorporated herein by reference. As illustrated in FIG. 1, a patient's heart 24 has been treated by deployment of an implant across a lower portion of the left ventricle 32 between septum 28 and a left wall or myocardium region 34. The implant generally includes a tensile member which extends between anchors 36 and 38.

A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. Each of these patents is also incorporated herein by reference.

While these and other proposed implants may help surgically remedy the size of the ventricle as a treatment of congestive heart failure and appear to offer benefits for many patients, still further advances would be desirable. In general, it would be desirable to provide improved devices, systems, and methods for treatment of congestive heart failure and other disease conditions of the heart. It would be particularly desirable if such devices and techniques could increase the overall therapeutic benefit for patients in which they are implanted, and/or could increase the number of patients who might benefit from these recently proposed therapies. Ideally, at least some embodiments would include structures and or methods for prophylactic use, potentially altogether avoiding some or all of the deleterious symptoms of congestive heart failure after a patient has a heart attack, but before foreseeable disease progression. It would be advantageous if these improvements could be provided without overly complicating the device implantation procedure or increasing the trauma to the patient undergoing the surgery, ideally while significantly enhancing the benefits provided by the implanted device.

BRIEF SUMMARY OF THE INVENTION

The present invention generally provides improved devices, systems, and methods for treating a heart of a patient. Embodiments of the invention may make use of structures which limit a size of a chamber of the heart, such as by deploying one or more tensile member to bring a wall of the heart and a septum of the heart toward each other (and often into contact). Therapeutic benefits of the implants may be enhanced by image-guided steering of the implant within the ventricle between penetration of the septum and wall. A plurality of tension members may help exclude scar tissue and provide a more effective remaining ventricle chamber. The implant may optionally be biodegradable, with the approximated surfaces of the septum and wall treated so as to induce the formation of adhesions. Antiproliferative agents or other drugs may be eluted from the implant to limit detrimental tissue responses and enhance the benefits of the implants for treatment of congestive heart failure and other disease states of the heart. Embodiments of this invention relate to devices and methods for completely off-pump treatment of congestive heart failure patients, particular sizing devices and methods for excluding infracted tissue and reducing ventricular volume. Some of the devices and methods described herein may be performed thoracoscopically off-pump and may be less traumatic to the patient than open chest and open heart surgical techniques.

In a first aspect, the invention provides a method for treating a heart. The heart has a first chamber bordered by a septum and a wall. The heart also has a second chamber that is separated from the first chamber by the septum. The method comprises penetrating the septum at a first location selected for deployment of an implant. The wall is penetrated at a second location selected for the deployment of the implant, with controlled steering being provided between the first location and the second location with reference to an image of the first chamber. The implant is deployed by affixing a first anchor of the implant adjacent the penetration of the septum, and a second anchor of the implant adjacent the penetration of the wall. Tension is applied between the first and second anchor.

The wall will often be penetrated at additional locations, with the tension being applied between the septum and the wall by a plurality of laterally offset tension members. While the tension members may be coupled to each other in some embodiments (such as by angling away from each other or the like), in most embodiments each implant will have its own associated anchors and tension member.

The tension members will generally bring the wall and septum into engagement, and the separation between the tension members will allow the engagement to extend across at least a portion of the chamber. This engagement can effectively exclude regions of the wall and septum from the left ventricle. The anchors may extend laterally along the septum or wall towards each other (for example, having a width as measured extending toward an adjacent anchor that is greater than a height). The pattern of implants and anchors will generally be arranged to leave a remaining effective chamber that approximates the shape of a healthy heart chamber, avoids excessive thrombus-accumulating voids, and provides good effective pumping of blood therethrough.

In many embodiments, tissue near the first or second location may be engaged and characterized by a probe. If the characterized tissue does not appear suitable for formation of the penetration, the probe may be repositioned at a more suitable location. For example, a probe having a distal electrode surface may be advanced into contact with the tissue, and a pacing signal can be transmitted from the electrode. If the pacing signal is directly coupled to healthy, contractile heart tissue, the probe has effectively characterized the engaged tissue. As it may be desirable for the penetration to be formed in healthy tissue in some embodiments, engaged tissues which are not effectively paced by the applied signal may not be suitable for locating the anchor. In other embodiments, it may be desirable for the penetration to be formed in scar tissue which is not as susceptible to pacing, so that the implant may not fully exclude all scar tissue from the effective chamber. In either case, tissue characterization may help improve accuracy over deployment of the implant and efficacy of the therapy. The probe may comprise a perforation device, and may also be used to perforate the characterized tissue such as by energizing a bullet-shaped electrode surface of a steerable perforation device with electrosurgical energy.

The anchors will often be affixed by radially expanding the anchors and engaging axially-oriented surfaces of the anchors with tissue adjacent the perforations. For example, one or more of the anchors may comprise a plurality of arms defined by axial cuts in a tube. Radial expansion of the anchors may be effected by bending the arms radially outwardly, with the axially oriented surface comprising a first portion of each arm that extends perpendicular to the axis of the tube, and which is supported by a longer angled portion of the arm. In some embodiments, the axially-oriented surface may be supported by introducing a fluid into the anchor, with the fluid often being restrained by a bladder material similar to a balloon of a catheter balloon. Such a bladder may be used to support radially expanding arms as described above, or may be used as an anchor by itself. The axially oriented surface does not necessarily have to be parallel to the axis of the tension member, and may angle radially outwardly while still providing sufficient axial tissue engagement for anchoring. The fill material may harden, reversibly or irreversibly, within the anchor. In some embodiments, the implant may release a bioactive material, such as by including a drug-eluting coating on at least a portion of the implant, by including pores in the bladder anchor which allow transmission of the bioactive agent from within the fill material, or the like. The agent may inhibit cell proliferation, enhance adhesion formation, and/or the like.

To promote formation of adhesions, a region of the endocardium bordering the first chamber may be treated by subjecting the region to mechanical injury, by applying electrical, laser, or some other energy, by applying an appropriate agent or compound, or the like. Where adhesions are promoted or otherwise affix the septum and wall to each other, the implant may biodegrade or be removed with scar tissue remaining effectively excluded from the chamber.

The tension may be applied between the anchors by decreasing a length of a tension member. As a result, a portion of the tension member may extend through the wall so as to remain in an extra-cardiac space. In general, the implant may be introduced through the wall and septum using a minimally invasive intraluminal approach, a minimally invasive endoscopic approach, an open surgical approach to the heart, or a combination of two or more of these methods. The image used for reference during deployment of the implant may be obtained using intracardiac echocardiography, extra-cardiac echocardiography, endoscopy, fluoroscopy, or the like. Preferably, the implant and/or delivery system components associated therewith will provide high contrasts within the image.

In another aspect, the invention provides a system for treating a heart. The heart has a first chamber bordered by a septum and a wall. The heart has a second chamber separated from the first chamber by the septum. The system comprises a plurality of implants. Each implant has an anchor, a wall anchor, and a tension member to apply tension between the septum and wall when the implant is deployed so as to bring the wall and septum into engagement. The implants together are configured to extend the engagement across a portion of the chamber (or all of the chamber) sufficiently to effectively exclude regions of both the wall and septum from the chamber.

In another aspect, the invention provides a system for treating the heart. The heart has a first chamber bordered by a septum and a wall, and a second chamber separated from the first chamber by the septum. The system comprises an implant having a septum anchor, a wall anchor, and a tension member to apply tension between the septum and wall when the implant is deployed so as to bring the septum and wall into engagement. A deployment catheter releasably supports at a least a portion of the implant for deploying the implant in the heart. The deployment catheter comprises or receives a tissue identifier for characterization of a tissue of the first chamber.

In another aspect, the invention provides a system for treating a heart having a first chamber bordered by a septum and a wall, and a second chambered separated from the first chamber by the septum. The system comprises an implant having a septum anchor, a wall anchor, and a tension member to apply tension between the septum and wall when the implant is deployed so as to bring the wall and septum into engagement. At least one of the anchors has a small profile insertion configuration and large profile deployed configuration. The at least one anchor is radially expandable from the small profile configuration to the large profile configuration in situ so that an axially-oriented surface of the at least one anchor can anchor the implant to tissue of the heart.

In yet another aspect, the invention provides a system for treating a heart having a first chamber bordered by a septum and a wall, and a second chambered separated from the first chamber by the septum. The system comprises an implant having a septum anchor, a wall anchor, and a tension member to apply tension between the septum and wall when the implant is deployed so as to bring the septum and wall into engagement. A deployment catheter releasably supports at least a portion of the implant for deployment of the implant in the heart. The deployment catheter comprises or receives an adhesion inducing surface for directing energy or a material toward a region of the endocardium bordering the first chamber. The material or energy induces adhesions along the region. The tension is applied so as to approximate the wall and septum along the region.

BRIEF DESCRIPTION OF THE DRAWINGS

FIGS. 4A-4E are cross-sectional views schematically illustrating methods for accessing, identifying, and penetrating tissues for deployment of the implant system of FIGS. 2 and 2A.

DETAILED DESCRIPTION OF THE INVENTION

The present invention generally provides improved devices, systems, and methods for treatment of a heart. Embodiments of the invention may be particularly beneficial for treatment of congestive heart failure and other disease conditions of the heart. The invention may find uses as a prophylactic treatment, and/or may be included as at least a portion of a therapeutic intervention.

Myocardial infarction and the resultant scar formation is often the index event in the genesis of congestive heart failure. The presence of the scar may, if left untreated, lead to a compensatory neuro-hormonal response by the remaining, non-infarcted myocardium. The systems, methods, and devices described herein may be applied to inhibit, reverse, or avoid this response altogether, often halting a destructive sequence of events which could otherwise cause the eventual failure of the remaining functional heart muscle.

Embodiments of the present invention may build on known techniques for exclusion of the scar and volume reduction of the ventricle. Unlike known techniques that are often accomplished through open surgery, including left ventricular reconstruction, ventricular restoration, the Dor procedure, and the like, the treatments described herein will often (though not necessarily always) be implemented in a minimally invasive manner. Embodiments of the invention can provide advantages similar to those (for example) of surgical reconstruction of the ventricle, resulting in improved function due to improved dynamics, and by normalizing the downward cycle initiated by the original injury and mediated by the neuro-hormonal disease progression response.

Advantageously, the methods, devices, and systems described herein may allow percutaneous left ventricular scar exclusion and ventricle volume reduction to be applied at any appropriate time during the course of the disease. Rather than merely awaiting foreseeable disease progression and attempting to alleviate existing cardiac dysfunction, the techniques described herein may be applied proactively to prevent some or all of the heart failure symptoms, as well as to reverse at least a portion of any existing congestive heart failure effects, to limit or halt the progression of congestive heart failure, and/or to retard or prevent congestive heart failure disease progression in the future. Some embodiments may, for appropriate patients, limit the impact of myocardial infarction scar formation before heart failure every develops.

Figure 1:
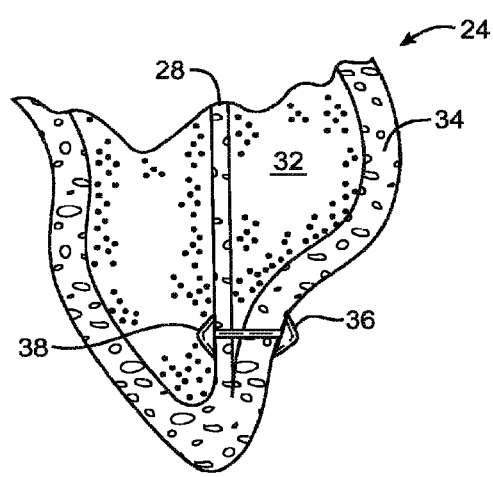
FIG. 1 is a cross-sectional view schematically illustrating a known implant and method for closing off a lower portion of a heart ventricle, as described in the background section.
Figure 2A:
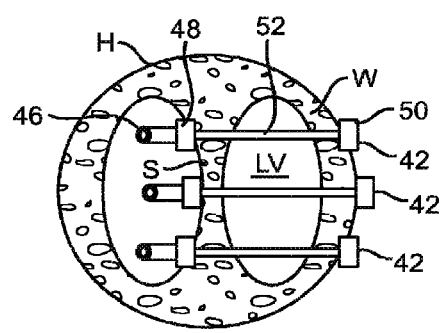
FIGS. 2A and 2B schematically illustrate deployment of three laterally offset implants to effectively exclude a portion of the left ventricle.
Figure 2B:
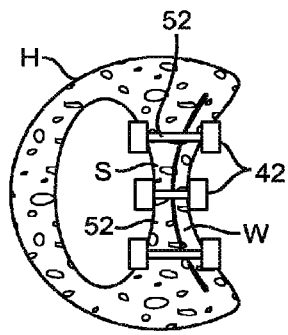
Figure 2C:
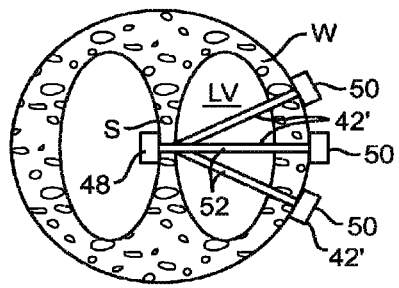
FIGS. 2C and 2D schematically illustrate a single implant having three laterally offset tension members for effectively excluding a region of scar tissue from the left ventricle.
Figure 2D:
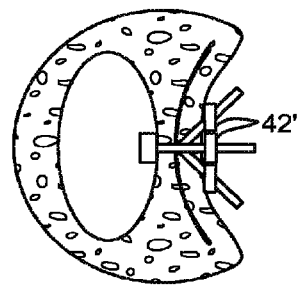
Figure 2:
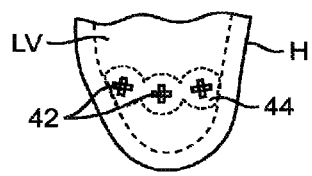
FIG. 2 schematically illustrates a side view of the lower portion of the heart, showing how three implants together reduce the effective size of the left ventricle by effectively excluding a region of scar tissue from the septum and left ventricle wall.

Referring now to the schematic illustration of FIG. 2, a side view of a lower portion of the heart H schematically illustrates how a size of the chamber of the heart can be limited using a plurality of implants. Implants 12 extend through the left ventricle (through the plane of illustration) so that only anchors of the implants are visible on the epicardial surface of the heart. By using a plurality of laterally offset anchors 12, a left ventricle LV is reduced from an initial size to a smaller effective size by engagement between the inner surfaces of the septum and left ventricle wall. A region of engagement 14 between these endocardial surfaces extends between the implants 12 and effectively excludes scar tissue along the lower portion of the septum and/or left ventricular wall from the functioning left ventricle. By arranging the implants 12 across some or all of the left ventricle, the remaining contractile tissue of the ventricle can make effective use of the reduced chamber volume to provide more effective pumping of the blood from within the heart, and may also avoid excessive stagnant voids that remain in fluid communication with the blood flow that might otherwise collect and release thrombus.

Referring now to FIGS. 2A and 2B, a schematic top view shows three laterally offset implants 42 that can be used to, in combination, effectively exclude scar tissue from left ventricle LV. In the illustration of FIG. 2A, each implant is shown in an elongate configuration. More specifically, each implant 42 extends distally from an associated deployment catheter 46 to a distal left ventricular wall anchor 50. A septal anchor 48 is coupled to the wall anchor 50 by a tension member 52. The tension member 52 of the implants 42 are offset laterally, with the tension members here shown extending roughly parallel to each other across the left ventricle LV. In other embodiments, the tension members may be disposed at an angle relative to each other, and may even extend across each other. Nonetheless, by positioning the anchors laterally offset of each other, effective exclusion of scar tissue from the left ventricle LV may be enhanced.

Referring now to FIG. 2B, implants 42 are shown fully deployed, with deployment catheters 46 detached from the implants and removed from the heart, and tension members 52 axially shortened from the elongate configuration of FIG. 2A to a shortened, tensioned configuration. Implants 42 in the shortened configuration draw endocardial surfaces of the wall W into engagement with the corresponding endocardial surfaces of septum S sufficiently to effectively exclude at least a portion of the scar tissue from the functioning lower ventricle. Note that the engagement need not be absolute along the entire cross section of the lower ventricle, so long as scar tissue is effectively excluded immediately after the procedure or, after an initial tissue response to the implant(s), at least some of the scar tissue is not subjected to the stress of being included in the pumping left ventricle. This may improve pumping efficiency of the remaining left ventricle and may limit disease progression from enlarged heart wall tissue stresses.

Referring now to FIGS. 2C and 2D, alternative implants 42' may also include a septal anchor 48 and a wall anchor 50, with a tension member 52 extending therebetween. Such alternative implants may, in some cases, have multiple wall anchors 50 associated with each septal anchor 48, or multiple septal anchors associated with each wall anchor. The tension members 52 may extend in positions that are both angularly and laterally offset from each other. As shown in FIG. 2D, axial shortening of the tension members between the anchors 48, 50 may leave a portion of the tension member extending into the extra-cardiac space. In some embodiments, one or a plurality of implants may provide a bunching engagement of endocardial tissues, with the engagement extending upon multiple fold lines so as to effectively exclude at least a portion of the scar tissue. Some or all of the components of the implants may be positioned using an epicardial access approach, with or without endocardial delivery or deployment catheters 46 (see FIG. 2A) for other implant components.

Figure 3A:
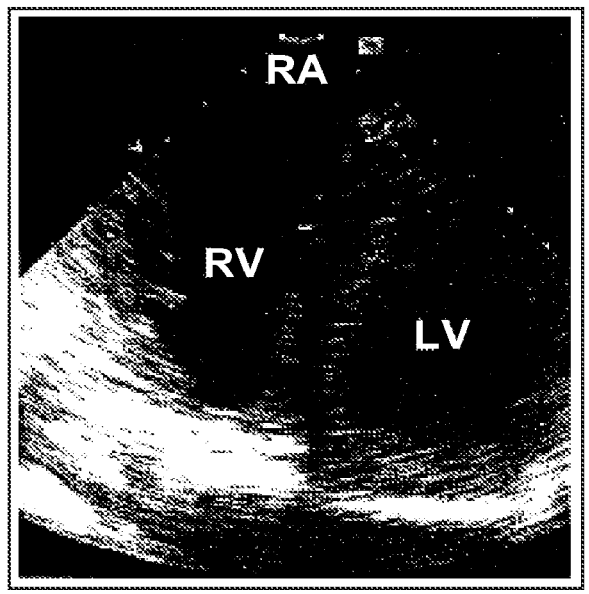
FIGS. 3A and 3B illustrate examples of images of the heart and/or devices disposed therein that may be used to direct deployment of embodiments of the invention.
Figure 3B:
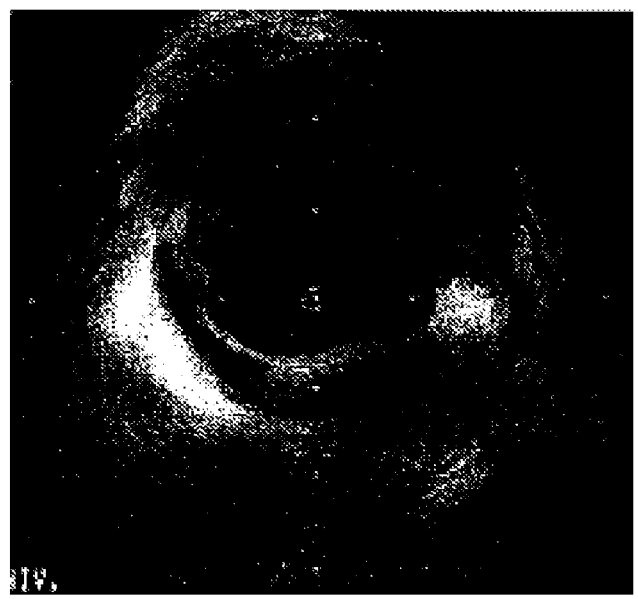

Referring now to FIGS. 3A and 3B, deployment of the implants described herein and implementation of the therapies will benefit from accurate and reliable identification of the margins separating the scar and viable, contractile myocardium. Such identification can be accomplished, for example, using pre-operative imaging, catheter-sensed activation potentials, pacing thresholds, ultrasonic imaging characteristics, biomarkers, or a variety of other tissue imaging and/or characterization methodologies. In general, it will be beneficial to provide information to the physician deploying the system to allow accurate characterization of selected locations as substantially comprising scar tissue or substantially comprising a viable contractile tissue. Additionally, the geometry of the chambers of the heart, and particularly the left ventricular chamber, should be clearly imaged to facilitate the desired reduction in size of the left ventricular chamber. This imaging may be accomplished by one imaging modality or by a combination of different imaging modalities. Exemplary imaging modalities which may be employed for identification of the heart geometry and/or tissue characterization include: echocardiography (including intracardiac echocardiography ("ICE") and/or extra-cardiac echocardiography (such as transesophageal echocardiography and/or transthoracic echocardiography ("TTE" and "TEE", respectively) or the like), intra- or extra-vascular endoscopy, fluoroscopy, or any of a variety of alternative existing or new imaging techniques, either alone or in combination.

FIGS. 3A and 3B illustrate an example of ICE showing the geometry of the heart chambers, including a right atrium RA, a portion of the right ventricle RV, and the left ventricle LV along with some of the heart tissues bordering these chambers. FIG. 3B illustrates an intracardiac echocardiography image in which a catheter device within the ventricle can be seen.

Deployment of the structures described herein may also benefit from sensors that can be used to monitor the procedure, such sensors ideally providing a real-time assessment of the progress of the treatment and performance of the heart during deployment and/or as deployment is completed. The goal of deployment will often be to achieve a desired reduction in size of a chamber (typically the left ventricle), while avoiding overcorrection (which might otherwise induce acute diastolic dysfunction). Such functional assessment sensors may comprise pressure sensors, hemodynamic sensing systems, strain sensors, oxygen saturation sensors, biological marker detectors, and/or other sensors measuring heart function to permit a quantitative assessment of efficacy of the procedure as it is implemented.

Referring now to FIGS. 4A-4E, exemplary techniques and structures for accessing and penetrating the septum and left ventricular wall can be understood. First summarizing these steps, it will be advantageous to identify, engage, and temporarily hold the device in alignment with a desired position on the right ventricular septum, as schematically illustrated in FIG. 4A. Identification or characterization of the engaged tissue will also be advantageous. The septum will be penetrated as can be understood with reference to FIG. 4B, and the system is steered across the left ventricular chamber as illustrated in FIG. 4C. The system engages one or more target locations on the left ventricular wall as shown in FIG. 4D. The engaged tissue may be characterized and the system repositioned as needed, with the system being held in engagement with the left ventricular wall if found to be at an appropriate or designated position, with the system optionally attaching or temporarily affixing itself to the left ventricular wall. The left ventricular wall may then be perforated, penetrated, or otherwise transcended as illustrated in FIG. 4E. As indicated above regarding FIGS. 3A and 3B, target tissue access, penetration, and implant deployment may be performed with reference to ICE within the blood stream of the vascular system, with the ICE images typically comprising 2-D sector images, the sectors often comprising an about 60 degree sector.

In more detail, referring now to FIG. 4A, an access and deployment system 70 includes a catheter 72 and a penetrating/sensing perforation device 74. In some embodiments, separate probes may be used for penetrating the heart tissues and characterizing the tissues. Here, catheter 72 accesses the right ventricle RV in a conventional manner, typically by advancing the catheter over a coronary access guidewire. A distal end of catheter 72 is aligned with a candidate location along the right ventricular surface of the septum S by a combination of axial rotation of the catheter and distal/proximal positioning of the catheter, as shown by the arrows. Positioning of the catheter is directed with reference to imaging (as described above) and when the end of the catheter is aligned with the candidate location a perforation device 74 is advanced distally so that a distal end of the perforation device contacts the septum S.

Perforation device 74 may characterize or verify that the candidate location is appropriate, for example, by determining a pacing threshold at the candidate site. Scar tissue ST may have a pacing threshold which differs sufficiently from a viable tissue VT to allow the physician to verify that the candidate site comprises scar tissue and/or is otherwise suitable. If the candidate site is not suitable, the perforation device 74 may be withdrawn proximally to disengage the perforation device from the septum S, and the catheter may be repositioned as described above to a new candidate site.

Catheter 72 may comprise a commercially available steerable sheath or introducer. Deflection of catheter 72 may be effected using one or more pull wires extending axially within the catheter body. Suitable introducers include devices that can be introduced transcutaneously into a vein or artery. Suitable steerable sheaths may generally comprise a tubular catheter body with an open working lumen. The open lumen can be used as a conduit for passing another catheter into the patient body, or for introducing another device (such as a pacing lead) into the patient body. Exemplary steerable sheaths for use in system 70 may include those commercially available from the Diag division of the St. Jude Corporation, from Medtronic, from Bard, and/or from others. Preferably, the working lumen of catheter 72 will be in a range from about 5F-11F. Alternative systems may employ a flexible sheath removably receiving a steerable catheter or other device therein, the steerable catheter optionally comprising a steerable electrophysiology catheter or a device derived therefrom. Still further embodiments may employ pre-bent cardiac access catheters.

Regarding perforating device 74, one embodiment would comprise a deflectable or steerable catheter body (ideally comprising a 2F-3F catheter) with a metallic rounded and/or bullet-shaped electrode at its distal end. The distal electrode is connected to a signal wire that terminates in a connector outside the body. Electrogram amplitudes recorded from the distal electrode can be used to help determine if the distal tip is located over scar tissue or over viable tissue. Efficacy in characterization of engaged heart tissues (between scar tissue and viable heart tissue) may be enhanced by recording the differential signal between the tip electrode and a band electrode located less than 1 cm from the distal electrode.

Pacing from the distal tip can be employed to help avoid perforation through viable myocardium. For most patients, such a perforation site would be counter-indicated. If the heart can be paced from the tip using a 10V amplitude pacing pulse, then viable myocardium will generally be disposed within about 5 mm of the tip. When the proper penetration site has been identified, then the distal tip is electrically coupled to an electrosurgical power source unit, and penetration is enabled by applying power to the tip in cut mode. At proper power settings, this perforation method can allow a clean perforation channel to be created without the tearing that can otherwise occur with physical perforation of the septum or free wall.

Once an appropriate site has been identified and verified, the system is held in alignment with the candidate site, and may optionally be affixed temporarily at the verified site. Perforation device 74 is advanced distally into and through septum S as illustrated in FIGS. 4B and 4C. Perforation device 74 may have a sharpened distal tip, a rotatable helical or screw structure, or other mechanical attributes to facilitate penetration into and perforation through the myocardium. Energy delivery elements (such as electrosurgical energy, laser energy, or the like) may also be provided. In some embodiments, system 70 may employ components similar to or modified from known septum traversing systems used for accessing the left ventricle. In general, it may be advantageous to seek to perforate tissue with an axis of perforation device 74 oriented across the ventricle and straight toward or near a suitable target site for the subsequent perforation, as imposing excessively acute angles on the heart tissue may weaken or even tear the heart tissue.

As can be understood with reference to FIGS. 4C and 4D, once perforation device 74 has penetrated through the septum S, manipulation of the catheter 72 under the guidance of the imaging system allows the perforation device to be steered across the left ventricle LV and into engagement with a target location along the wall of the left ventricle. The tissue at this target location may be characterized using a sensor of perforation device 74, pacing of the engaged tissue, or the like, and the end of the perforation device repositioned as needed. The preferred location for deployment of the implant may be along or adjacent to scar tissue ST. In some embodiments, system 70 may be used for positioning of a lead at a location separated from the axis of the implant tensioning member. System 70 also allows for epicardial lead placement by advancing the perforation device 74 endocardially through septum S and the myocardium of the left ventricular wall W until it is located on the epicardial surface of the heart. The perforation device 74 and/or lead may be at least temporarily fixed at that location and tested for proper pacing effect, as can be understood with reference to FIGS. 4E and 5B.

The access and deployment system 70 described above with reference to FIGS. 4A-4E may be supplemented with or replaced by a number of differing system components. For example, as can be understood with reference to FIG. 5A, a balloon catheter 80 or other sealing structure may be used, optionally being advanced within catheter 72 and/or over perforation device 74. The balloon of balloon catheter 80 may be positioned within the myocardium of septum S or the left ventricular free-wall W to anchor the deployment system temporarily to the heart tissue and control blood loss, particularly blood loss through the left ventricular wall into the extra-cardiac space. In some embodiments, two separate balloons may be used to seal both the septum and the left ventricular wall. Balloons may also be used with or as anchors of the implant device.

Still further alternative structures may be employed, perforation device 74 may have any of a variety of sensors, including pressure sensors and the like. System 70 will often comprise high contrast structures to enhance imaging, such as by including materials having high radio-opacity, echo-density, or the like. As noted above, perforation device 74 may have or be used with a cutting, drilling, or other mechanism to help in tissue penetration. Still further alternative structures may be used for steering and positioning of the deployment system and perforation device. For example, rather than manually manipulating or steering catheter 72 to position and orient the implant, the deployment system may employ robotic surgical techniques such as those now being developed and/or commercialized for manipulation of catheters. Magnetic steering of the catheter end may also be employed, and any of a wide variety of mechanical steerable or preformed catheter structures could be employed. Some or all of the components may access the left and/or right ventricular chambers using an epicardial approach, rather than the endovascular approach described above. A combination of an extra-cardiac and intracardiac approach may also be employed, with the components of the implant being introduced in any of a wide variety of techniques. In some embodiments, implant 42 and/or other components of the system may be deployed in an open surgical procedure. Directly accessing at least the epicardial surface of the heart may significantly facilitate positioning and deployment of implant 42, particularly for development of implant system components and techniques, including those which may later be deployed in a minimally invasive manner.

Figure 5B:
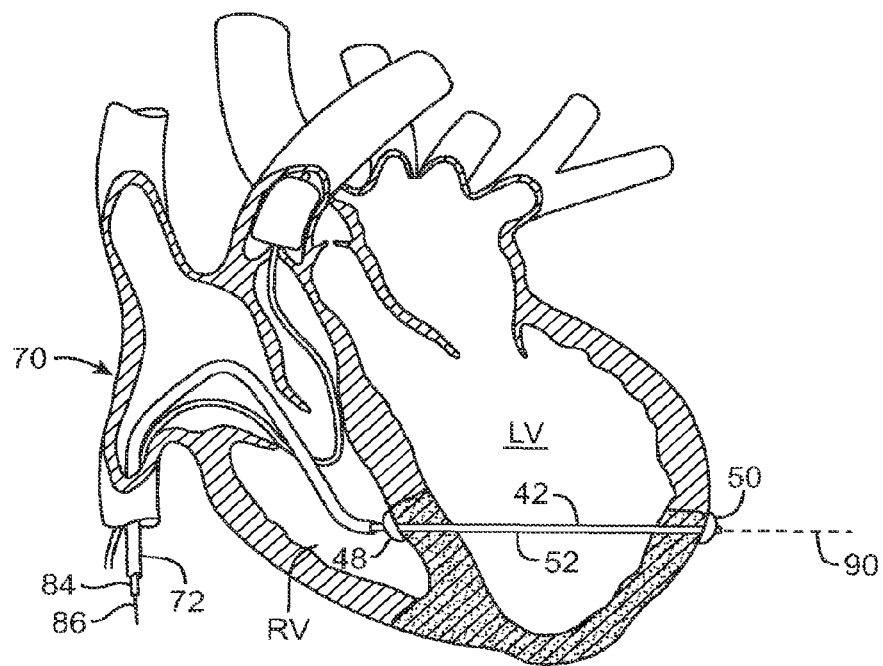
FIGS. 5A and 5B are cross-sectional views schematically illustrating initial deployment of an implant of the system of FIGS. 2A and 2B, with the implant initially being deployed in an elongate configuration.
Figure 6A:
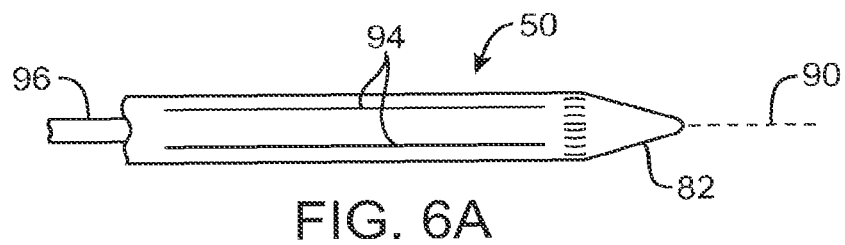
FIGS. 6A-6D illustrate deployment of an anchor for use in the implant of FIG. 5B.
Figure 6B:
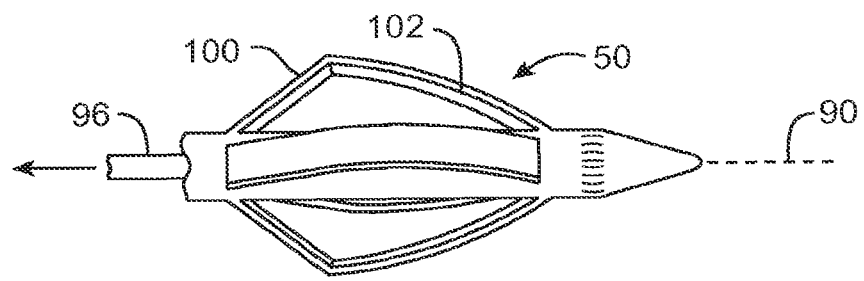
Figure 6C:
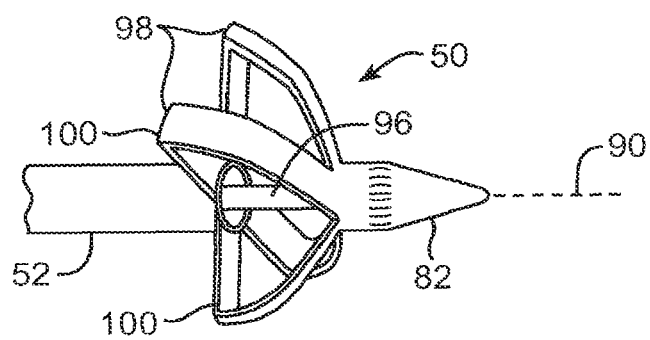

Referring now to FIGS. 5B and 6A-6C, implant 42 is deployed through catheter 72 of deployment system 70, with the implant initially being deployed in an elongate configuration extending across left ventricle LV. Anchors 48, 50 of implant 42 advance distally through a lumen of catheter 72 while the anchor is in a small profile configuration, as illustrated in FIG. 6A. Anchor 50 expands from the small profile configuration to a large profile configuration, which may be effected by altering a distance between a distal end 82 and a shaft of tension member 52 using elongate bodies 84, 86 detachably coupled to the distal end 82 and tension member 52, respectively.

Figure 6D:
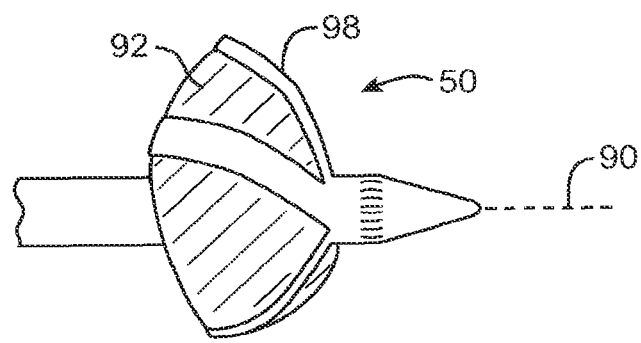

In general, anchors 48, 50 will be deployable through, over, or adjacent to the myocardium tissue penetrating components of deployment system 70. The anchors will attach to or otherwise engage the wall, usually by expanding or inflating into a cross section larger than that of the penetration through the heart tissue. A wide variety of anchor structures may be employed, including structures that form a disk-shaped surface or lateral extensions from an axis 90 of implant 42. As can be understood with reference to FIG. 6D, an inflatable bladder 92 or balloon of appropriate shape may be used alone or in combination with other anchoring structures. If an inflatable bladder or balloon is used, it may be filled with a substance which is initially introduced as a liquid, but which reversibly or irreversibly solidifies. Suitable fill materials may, for example, comprise liquid silicone rubber, which can polymerize at any of a variety of alternative desired rates depending on the chemistry of the material used. Optionally, the material may solidify over more than one hour, optionally over many hours or even days at body temperatures. During a procedure, such an injected liquid could be removed if desired, but the material would eventually solidify. Biological adhesives could also be delivered as fluid to fill a balloon, though cure times are relatively shorter for such materials. Such materials would irreversibly solidify.

The septal and left ventricular wall anchors 48, 50 may be identical or similar in structure, or may differ to reflect the differences between the epicardial and endocardial surfaces they engage. Fixation to the wall and septum will generally be sufficient to support the tension of tensile member 52, which will generally be capable of approximating the wall and septum, typically maintaining proximity or engagement between these structures during beating of the heart. Anchors 48, 50 and tensile member 52 will often comprise high-contrast materials to facilitate imaging, such as by including materials of sufficient radio-opacity, echo density, and the like.

In some embodiments, implant 42 may be used alone or with similar implants to effect volume reduction over a length, width, or volume of the ventricular wall. When at least a portion of the implant 42 is deployed using an epicardial approach, left ventricular anchor 50 will often be included in the components attached from outside the heart, with tensile member 52 and/or anchor 48 being attached to this epicardial component during deployment. Robotic structures may be used to position the intracardiac or extra-cardiac components, and/or to attach the two of them together.

Referring again to FIGS. 6A-6D, the exemplary anchor structure comprises a Nitinol™ shaped memory alloy or other flexible material formed into a tubular shaft. Axial cuts 94 may be formed along this tubular shaft, with the cuts having a desired length and being disposed near distal end 82. Anchor 50 is advanced until the most proximal margin of cuts 94 extends clear of the heart tissue. A retraction member 96 (optionally being releasable attached to the associated elongate body 86) fixed to the inside of distal end 82 is refracted proximally, expanding the walls of the tubular shaft radially into the circumferential series of arms 98. Tissue engaging surfaces 100 of arms 98 may be substantially perpendicular to axis 90 of the implant. Arms 98 may have two general components, including the portion of the arm along tissue engaging surface 100 and a slightly longer bracing portion of the arm 102 extending away from the tissue engaging surface along axis 90. The proportionate sizes of these two elements of arms 98 may be pre-determined by localized altering of the arm stiffness (effecting the placement of living hinges) or the tubing material will otherwise preferably bend so that the arms assume a desired shape. The deployed arms may have, for example, the pyramid shape shown with the tissue engaging surface 100 supported by angled portions 102 with a pyramid-like force distribution, the angled bracing portions forming a triangular relationship with the surface of the heart wall.

Member 96 may remain within the deployed anchor, axially affixing tensile member 52 relative to the end of the anchor after deployment of the implant. This can help inhibit collapse of the arms 98. In some embodiments, arms 98 may be biased to the large cross section deployed configuration, such as by appropriate treatments to a shape memory alloy or the like. In such embodiments, member 98 or some other actuation structure may restrain the anchor in a small cross section configuration, it may not remain within the deployed implant after it is expanded.

As can be understood with reference to FIG. 60, once the anchor 50 is deployed and in position, additional support elements may be positioned or deployed through the deployment system 70. For example, a space occupying or expandable structure such as bladder 92 may be positioned or inflated within arms 98, internal support structures (optionally comprising internal pyramid-like support arms) may be deployed. The septal anchor 48 will optionally have a structure similar to anchor 50, with the proximal and distal orientations of the arm structures reversed.

While anchor 50 of FIGS. 6A-6D is shown as being integrated into a tubular shaft of elongate tensile member 52, the anchor or fixation device may alternatively comprise a separate element introduced separately over a guidewire or the like. Still further alternatives may be employed, including fixation of the heart walls by placement of magnetic materials on or within the walls, with the bodies acting as anchors and the magnetic material acting as a tensile component so as to hold the walls in apposition.

Anchors 48 and/or 50 may optionally be drug eluting. For example, bladder or balloon 92 may have a porous surface capable of eluting a substance from the film material. Alternatively, an outer surface of the balloon or the anchor structure itself may comprise a permanent or biodegradable polymer or the like, such as those that have been developed for drug eluting stents and available from a number of commercial suppliers. Drugs eluted from the implants may include any of the compositions eluted from drug-eluting stents.

Figure 5A:
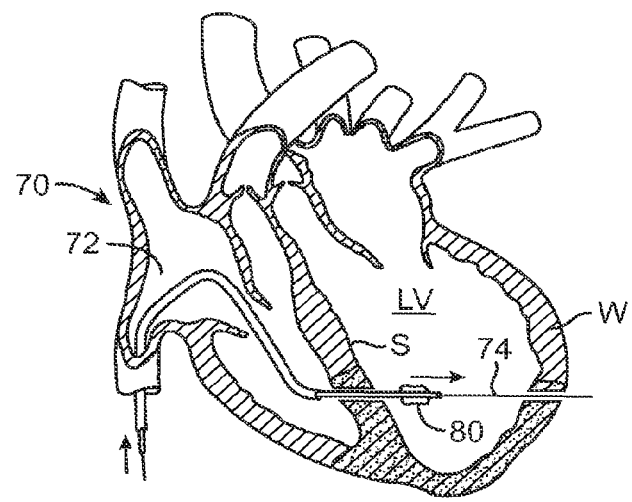
Figure 7B:
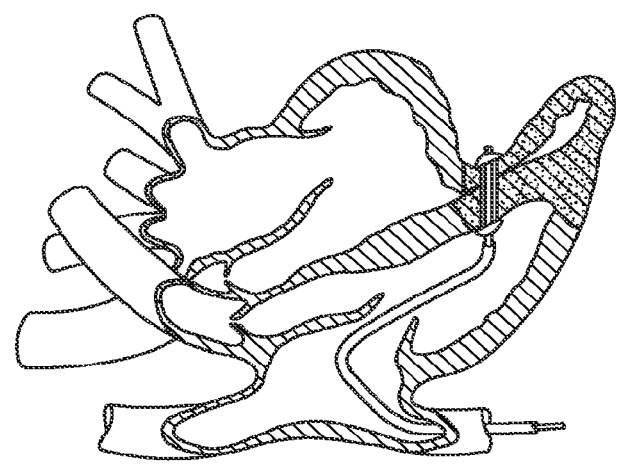
FIGS. 7A and 7B are cross-sectional views schematically illustrating shortening of the tensile member of FIG. 5B from the elongate initial configuration to a shortened deployed configuration so as to reduce a size of the left ventricle and effectively exclude at least a portion of a scar tissue from the left ventricle.
Figure 7A:
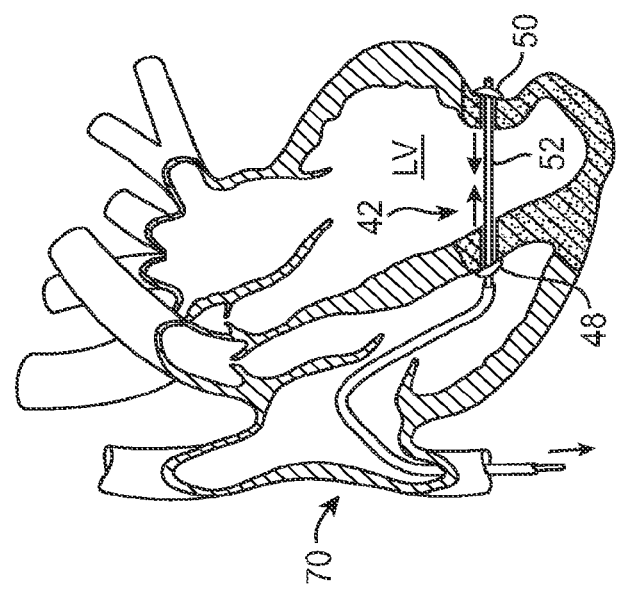

Referring now to FIGS. 5B, 7A, and 7B, after anchors 48-50 are deployed, implant 42 may be shortened from its elongate configuration with a relatively large distance between the anchors along tensile member 52 to a shortened configuration. In some embodiments, the tensile member may comprise a shaft of the tissue penetrating perforation device 74 (see FIGS. 4A-4E). In other embodiments, tensile member 52 will comprise a separate structure. In many embodiments, the tensile member and anchors will remain permanently in the heart to hold the septum and left ventricular wall in apposition. To allow shortening of the tensile member, excess length of the tensile member may be removed with the catheter 72 and other components of the delivery system, and/or some portion of the length of the tensile member may remain in the extra-cardiac space outside the left ventricular wall.

Optionally, a ratchet mechanism may couple the septal anchor 48 to the tensile member 52, with the ratchet mechanism allowing the separation distance between the anchors to gradually decrease. While exemplary ratchet mechanisms are described below with reference to FIGS. 11A-11C, 12A and B, and 14A-14C, a wide variety of alternative structures that can be reconfigured in situ to alter the separation distance between the anchors might alternatively be employed.

Figure 8:
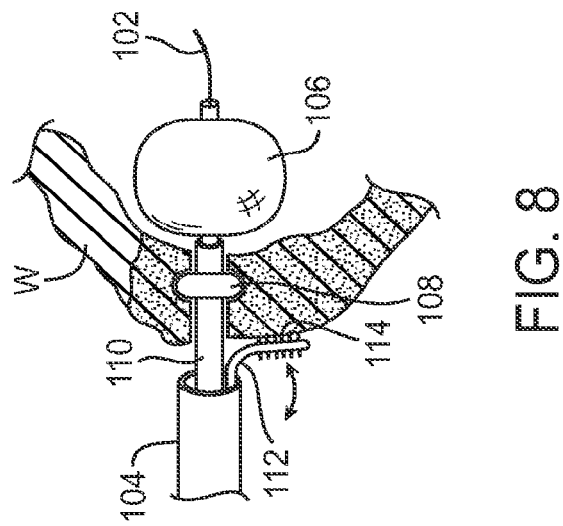
FIG. 8 schematically illustrates an alternative anchor structure in the form of a inflated balloon, an annular balloon disposed within a wall of the left ventricle so as to inhibit bloodflow through a perforation, and treating a myocardial tissue surface with mechanical energy from a bur or the like to promote adhesion formation.

Referring now to FIG. 8, additional optional elements for the implants and/or deployment systems described herein can be understood. Here, a guidewire 102 is shown extending through a perforation of left ventricular wall W, with components of the deployment system and/or implant advanced over the guidewire. A deployment catheter sheath 104 may be used with or without guidewire 102. Guidewire 102 and/or sheath 104 may be steerable to facilitate access and deployment of the implant.

A temporary or permanent anchor is here provided by a balloon 106. An axially-oriented portion of the outer surface of balloon 106 engages the adjacent epicardial surface of wall W to pull the wall towards engagement with the septum, as described above. Balloon anchor 106 may comprise a structure similar to a balloon of a balloon catheter, with an expandable and biocompatible bladder material defining the balloon wall. Along with the exemplary fill materials described above, the fill material may generally comprise a reversibly or irreversibly hardenable polymer, and the bladder material may have pores to allow eluting of drugs from the fill material or fluid.

An annular expandable structure such as annular balloon 108 on an associated catheter 110 may expand within the myocardium from the perforation or penetration through the left ventricular wall W or septum S. Balloon 108 may help to temporarily hold the deployment system in position relative to the perforation and tissue structures, or may in some embodiments be used as a permanent anchor (with or without additional anchoring structures). Temporary deployment of balloon 108 against the myocardial tissues may be particularly advantageous during or after perforation of the free left ventricular wall W during deployment of the wall anchor, as it may help to limit the release of blood into the extra-cardiac space. Balloon 108 may comprise a relatively standard balloon catheter material, such as nylon, PET, or the like.

Yet another aspect schematically illustrated in FIG. 8 is a probe 112 having a surface 114 that treats the endocardial surface of the left ventricle wall W or septum S so as to promote formation of adhesions. Surface 114 may comprise a bur or other mechanical energy application surface for imposing mechanical trauma on the tissues within the heart. In alternative embodiments, surface 114 may comprise an electrode surface for applying electrosurgical energy, light refracting surface for applying visible or invisible radiation, one or more agent delivery ports for transmitting caustic or sclerosing agents to the heart tissue, or the like. Such surfaces may apply a controlled, limited trauma to the tissue surface regions of the left ventricular wall and/or septum so as to induce the formation of scar tissues bridging these two tissue structures and forming permanent adhesions therebetween.

When a probe 112 or surface of the implant or delivery catheter is used to promote formations of adhesions, or when the implant provides sufficient compressive force between the left ventricular wall and septum so as to promote adhesions without separately imposing a trauma on the tissue surface, some or all of the implant may comprise biodegradable material. After the adhesions are fully formed and the biodegradable material of the implant degrades, the natural adhesions may alone maintain the reduced size of the left ventricle, exclude scar tissue from the effective left ventricle, and limit the effects of congestive heart failure. Suitable biodegradable materials for use in the structural components of the implants described herein may include materials developed for and/or used in biodegradable stent structures.

While an myocardial engagement balloon 108, balloon anchor 106, and trauma inducing probe 112, are shown schematically together in FIG. 8, and while some embodiments of the methods and systems described herein may make use of all three of these components, many embodiments may employ only any one or any two of these optional structures. Additionally, while much of the above-description relates to intravascular access and deployment of at least a portion of the implant, other embodiments may be deployed during laparoscopic or even open heart surgery. Such embodiments may be particularly beneficial for verification and tailoring of the pattern of multiple implants to be used for scar tissue exclusion and left ventricular volume reduction, with subsequent embodiments making use of the verified and/or refined patterns through an at least partially intravascular approach.

Figure 9:
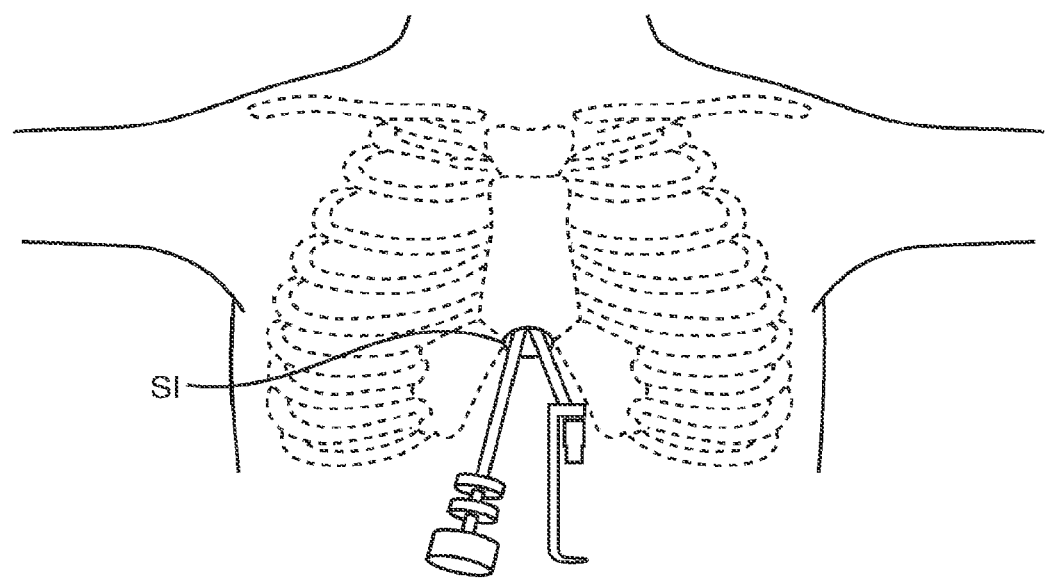
FIG. 9 schematically illustrates accessing the heart via a subxiphoid incision.
Figure 10:
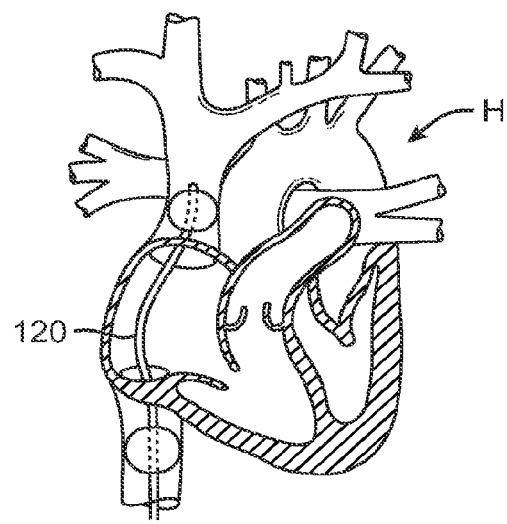
FIG. 10 illustrates a method for unloading of the heart with a double balloon catheter.

Referring now to FIG. 9, embodiments of the invention may be deployed using a subxiphoid incision SI to access the heart, and/or the ventricles of the heart. In some embodiments, additional access may be obtained through one or more intercostals space for one or more instruments. As shown in FIG. 10, a double balloon catheter 120 may optionally be used to unload the heart tissue. Double balloon catheter 120 can provide inflow occlusion to decompress the ventricles, thereby reducing the systolic pressure. This may aid in reducing the ventricular volume and/or in the exclusion of dysfunctional cardiac tissue. Double balloon catheter 120 may optionally be placed using open chest surgery. Alternatively, double balloon catheter 120 may be positioned using minimal invasive techniques, such as via a femoral or subclavian vessels or veins, and optionally being positioned percutaneously.

In some embodiments, double balloon catheter 120 may be positioned so that one balloon is in the superior vena cava and one balloon is in the inferior vena cava, thus blocking most or even essentially all blood flow from the body back to the heart. It may be easier to insert the balloon catheter either into the jugular vein or the femoral vein than it is to place using a cardiac insertion site. An alternative (and in at least some cases faster) way of off-loading the left heart is to inflate a suitably large compliant balloon in the pulmonary artery just above the pulmonic valve (proximal to the branching into the left and right pulmonary arteries). A partially inflated balloon will tend to float into the pulmonary artery from the right atrium, since blood flow carries it into that position. Hence, this may provide another method of decreasing preload on the ventricle.

Figure 11A:
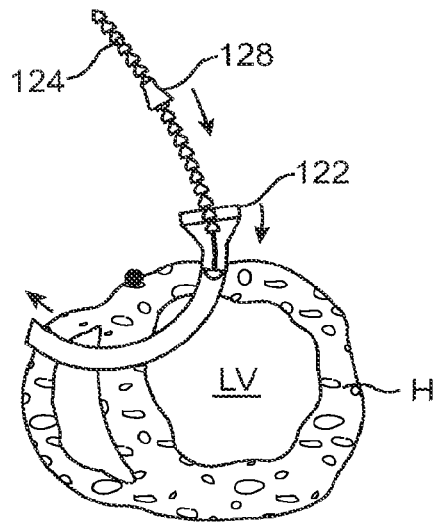
FIGS. 11A-11C schematically illustrate one variation of a transventricular implant and anchor system from a left ventricular approach.
Figure 11B:
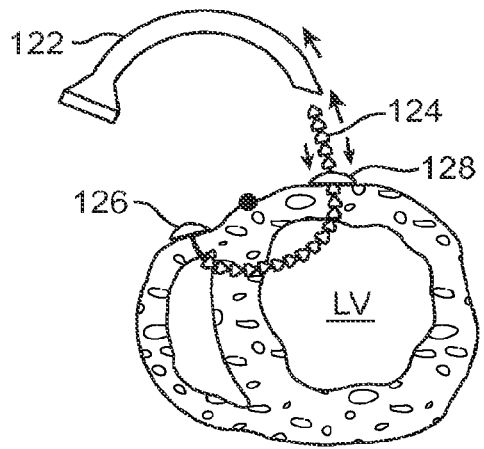
Figure 11C:
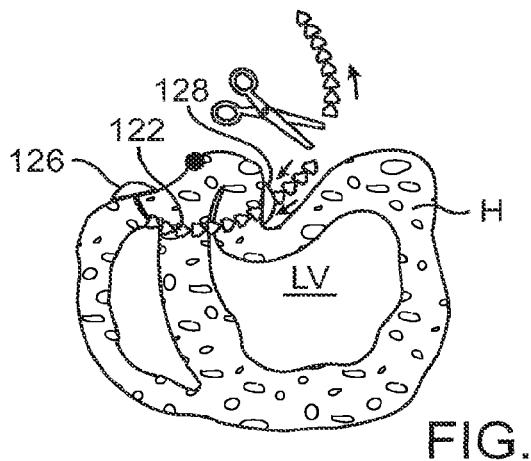

With reference to FIGS. 11A-11C, one variation of a transventricular implant and anchor system deployment from a left ventricular LV approach. A sharpened, curved tissue piercing tubular body 122 pierces the left ventricular wall, the septum, and extends back out through the right ventricular wall. This allows a ratcheted tension member 124 to be introduced through the tissues of the heart within a lumen of tubular body 122, with a first anchor 126 being attached to the tension member after insertion through the tubular body and expanded as described above or affixed after the distal end of the tension member extends free of the heart tissue. Regardless, once the tension member extends into and/or through both ventricles, the tubular body 122 can be withdrawn proximally and a second anchor 128 can be moved distally along the tension member to engage the myocardial surface of the heart, as seen in FIG. 11B. Second anchor 128 may optionally pass through the lumen of tubular body 122 and expand radially, or may be coupled to tension member 124 after the tubular body is withdrawn.

An exemplary ratcheting interface between tension member 124 and second anchor 128 may make use of a series of radial protrusions and/or detents disposed along an axis of the tension member. For example, the tension member may have slide surfaces which taper radially outwardly distally along the tension member to allow the anchor interface to slide sequentially over the slide surfaces in a distal direction, and detent surfaces which are oriented distally to engage corresponding proximally oriented surfaces of the anchor interface so as to inhibit proximal movement of the anchor relative to the tension member. Second anchor 128 may have a ratchet interface structure including (or derived from) the sealing components of a Touhy-Borst valve structure. Such an interface may resiliently deflect to pass the slide surfaces of the tension member and may grab or engage the detent surface when the tension member is pulled distally. Such a valve structure may also be increased in diameter to release the tension member if desired and/or tightened towards its smallest diameter to immovably (and optionally permanently) affix the anchor relative to the tension member. Exemplary embodiments of ratcheting tension member 122 may comprise polymers or metals, optionally comprising a polyester such as Mylar®, a thermoplastic such as Nylon™, a stainless steel, a shape memory allow such as Nitinol™, or the like.

As shown in FIG. 11C, second anchor 128 can be positioned along tension member 122 so as to effectively exclude scar tissue from the left ventricle and/or reduce a volume of the left ventricle. Some portion of tension member 122 may be disposed within the right ventricle, right ventricle scar tissue may be excluded, and/or the volume of the right ventricle may also be reduced. The tension member may be severed using a blade or the like as shown schematically, though some of the tension member may extend into the extracardiac space. In alternative embodiments using different surgical approaches (such as when using the catheter-based systems described above), at least a portion of the tension member may extend into the right ventricle or the like.

Figure 12A:
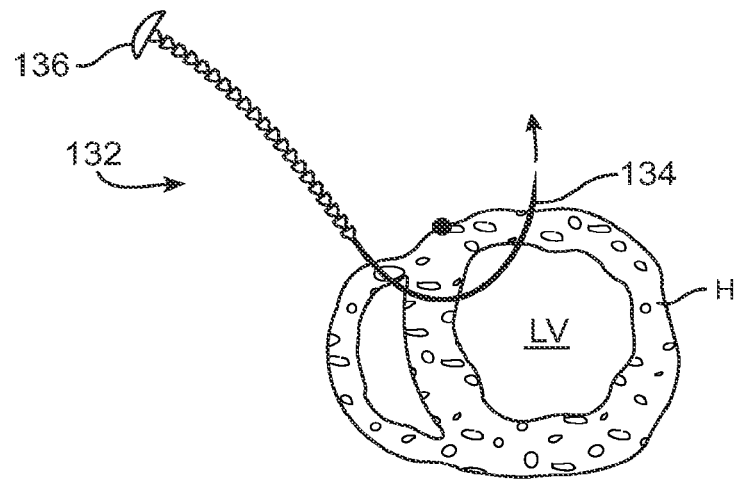
FIGS. 12A and 12B schematically illustrate another variation of a transventricular implant and anchor system from a right ventricular approach.
Figure 12B:
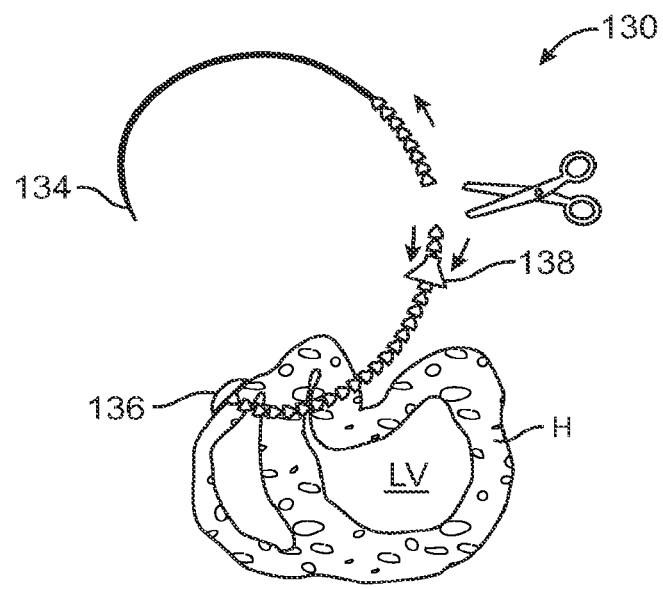
Figure 13:
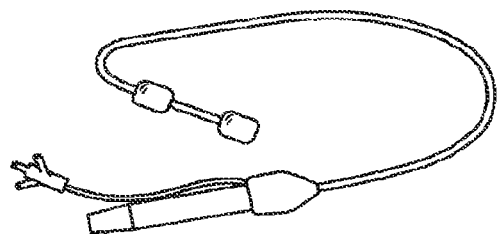
FIG. 13 illustrates a double balloon catheter for unloading of the heart in the method of FIG. 10.
Figure 14A:
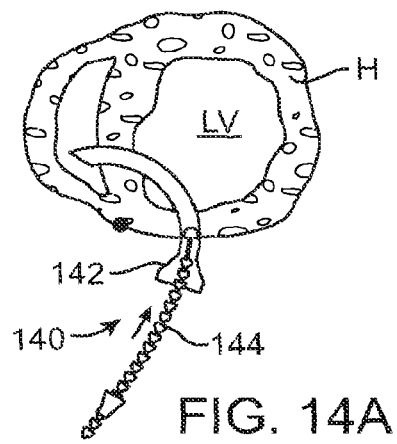
FIGS. 14A-14C schematically illustrate another variation of a transventricular implant and anchor system from a left ventricular approach.
Figure 14B:
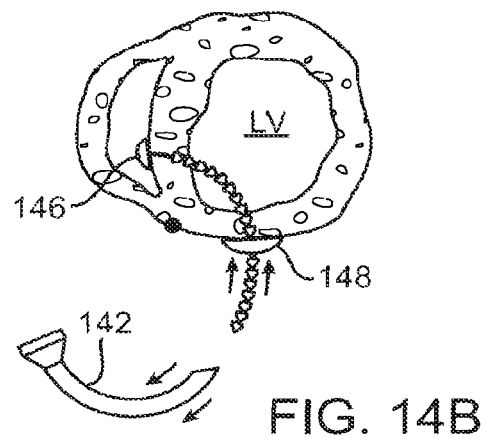
Figure 14C:
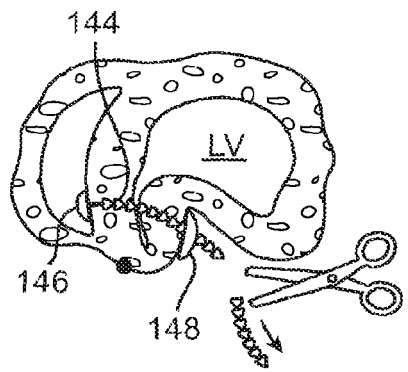

Referring now to FIGS. 12A and 12B, another alternative embodiment of an implant 130 and deployment system makes use of a transventricular approach from the right ventricle. A curved tension member 132 having a distal tissue penetrating end 134 and a proximal anchor 136 affixed thereto is introduced through the wall of the right ventrical, through the septum, across the left ventricle LV, and out through the left ventricular wall. The tension member 132 and affixed anchor 136 are advanced distally so that the anchor engages the surface of the heart, and a second anchor 138 is attached by passing distal end 134 through the anchor. Second anchor 138 is ratcheted proximally along tension member 132 to exclude scar tissue and limit a size of the left ventricle, with the distal end and at least a portion portion of the tension member that is distal of the positioned anchor being severed and removed from the deployed implant. FIG. 13 shows an exemplary double balloon catheter for use as described above with reference to FIGS. 9 and 10. FIGS. 14A-14C schematically illustrate another transventricular anchor system and deployment from a surgical site outside the heart similar to that of FIGS. 11A-11C, using a tubular body 142 to position a tension member 142 to which first and/or second anchors 146, 148 are ratchetably affixed.

It should be noted that the systems and methods described herein for excluding scar tissue and reducing a size of a chamber of the heart may make use of a plurality of different implants of different types and even different surgical approaches. For example, while systems may include a plurality of implants deployed from a site outside the heart (such as the embodiments shown in FIGS. 11A-11C, 12A and B, and 14A-14C), alternative systems may include one or more implants of one or more types deployed from outside the heart, along with one or more implants of one or more types deployed from inside the heart using a blood-vessel approach. Systems with a plurality of implants deployed from outside and/or inside the heart may benefit from any of a variety of imaging techniques so that the implant systems effectively exclude scar tissue and limit a size of one or more heart chamber.

While exemplary embodiments have been described in some detail for clarity of understanding and by way of example, a variety of modifications, adaptations, and changes will be obvious to those of skill in the art. Hence, the scope of the invention is limited solely by the appended claims.

What is claimed is:

1. A method for treating a heart, the heart having a first chamber bordered by a septum and a wall, wherein the chamber comprises a left ventricle of the heart, the heart having a second chamber separated from the first chamber by the septum, the method comprising:
penetrating the septum at a first location;
penetrating the wall at a second location;
penetrating the wall at a third location that is laterally offset from the second location;
affixing a first anchor adjacent the penetration of the septum;
affixing a second anchor adjacent the penetration of the wall at the second location, wherein a first tension member extends from the first anchor to the second anchor and tensionalby couples the first anchor and the second anchor;
affixing a third anchor adjacent the penetration of the wall at the third location, wherein a second tension member extends from the first anchor to the third anchor and tensionalby couples the first anchor and the third anchor such that a plurality of anchors positioned adjacent the wall are tensionably coupled with the first anchor;
applying tension between the first anchor, the second anchor, and the third anchor by tensioning the first tension member and the second tension member so that tension is applied between the septum and the wall;
wherein the first anchor, the second anchor, and the third anchor are tensioned sufficiently to bring the wall and septum into engagement, and wherein the second and third anchors are separated so as to, in combination, extend the engagement across a portion of the wall sufficiently to effectively exclude regions of the wall and septum from the left ventricle with scar tissue extending along the excluded regions.

2. The method of claim 1, wherein the third anchor is angularly offset from the second anchor.

3. The method of claim 1, further comprising engaging tissue near the first location or the second location with a probe to characterize the engaged tissue with the probe.

4. The method of claim 3, wherein the engaged tissue is characterized by pacing the engaged tissue with an electrode of the probe.

5. The method of claim 1, wherein the anchors are affixed by radially expanding the anchors and engaging axially-oriented surfaces of the anchors with tissue adjacent the perforations.

6. The method of claim 1, wherein at least one of the anchors comprises a plurality of arms that are deployable against the surface of the septum or wall.

7. The method of claim 1, further comprising inducing adhesions between the wall and the septum by treating a region of endocardium bordering the first chamber, the tension being applied so as to approximate the wall and the septum along the endocardium region.

8. A method for treating a heart, the heart having a first chamber bordered by a septum and a wall, wherein the chamber comprises a left ventricle of the heart, the heart having a second chamber separated from the first chamber by the septum, the method comprising:
penetrating the septum;
penetrating the wall at a first location;
penetrating the wall at a second location that is laterally offset from the first location;
affixing a septal anchor adjacent the penetration of the septum;
affixing a first wall anchor adjacent the penetration of the wall at the first location, wherein a first tension member extends from the septal anchor to the first wall anchor;
affixing a second wall anchor adjacent the penetration of the wall at the second location, wherein a second tension member extends from the septal anchor to the second wall anchor;
applying tension between the septal anchor and the first and second wall anchors via the first and second tension members to apply tension to the septum and the wall.

9. The method of claim 8, wherein the second wall anchor is angularly offset from the first wall anchor.

10. The method of claim 8, further comprising engaging tissue near the septum or the wall with a probe to characterize the engaged tissue with the probe.

11. The method of claim 10, wherein the engaged tissue is characterized by pacing the engaged tissue with an electrode of the probe.

12. The method of claim 8, wherein the septal anchor, first wall anchor, and second wall anchor are affixed by radially expanding said anchors and engaging axially-oriented surfaces of the anchors with tissue adjacent the perforations.

13. The method of claim 8, wherein at least one of the septal anchor, first wall anchor, or second wall anchor comprises a plurality of arms that are deployable against the surface of the septum or wall.

14. The method of claim 8, further comprising inducing adhesions between the wall and the septum by treating a region of endocardium bordering the first chamber, the tension being applied so as to approximate the wall and the septum along the endocardium region.

15. A method for treating a heart, the heart having a first chamber bordered by a first wall and a second wall, the method comprising:
penetrating the first wall;
penetrating the second wall at a first location;
penetrating the second wall at a second location that is laterally offset from the first location;
affixing a first anchor adjacent the penetration of the first wall;
affixing a second anchor adjacent the penetration of the second wall at the first location;
coupling a first tension member with the first anchor and the second anchor, the first tension member being tensionable to apply tension to the first wall and the second wall at the first location via the first anchor and the second anchor;
affixing a third anchor adjacent the penetration of the second wall at the second location; and
coupling a second tension member with the first anchor and the third anchor, the second tension member being tensionable to apply tension to the first wall and the second wall at the second location via the first anchor and the third anchor.

16. The method of claim 15, wherein the third anchor is angularly offset from the second anchor.

17. The method of claim 15, further comprising engaging tissue near the first wall or the second wall with a probe to characterize the engaged tissue with the probe.

18. The method of claim 17, wherein the engaged tissue is characterized by pacing the engaged tissue with an electrode of the probe.

19. The method of claim 15, wherein the first anchor, second anchor, and third anchor are affixed by radially expanding said anchors and engaging axially-oriented surfaces of the anchors with tissue adjacent the perforations.

20. The method of claim 15, wherein at least one of the first anchor, second anchor, or third anchor comprises a plurality of arms that are deployable against the surface of the first wall or second wall.

* * * * *